(12) United States Patent
Teshigahara et al.

(10) Patent No.: US 7,632,777 B2
(45) Date of Patent: Dec. 15, 2009

(54) COMPOSITE OXIDE CATALYST AND METHOD FOR PREPARATION THEREOF

(75) Inventors: Isao Teshigahara, Mie (JP); Nariyasu Kanuka, Mie (JP); Tomoatsu Iwakura, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 472 days.

(21) Appl. No.: 10/495,071

(22) PCT Filed: Nov. 8, 2002

(86) PCT No.: PCT/JP02/11703

§ 371 (c)(1),
(2), (4) Date: Sep. 29, 2004

(87) PCT Pub. No.: WO03/039744

PCT Pub. Date: May 15, 2003

(65) Prior Publication Data

US 2005/0033093 A1 Feb. 10, 2005

(30) Foreign Application Priority Data

| Nov. 8, 2001 | (JP) | 2001-343440 |
| Nov. 9, 2001 | (JP) | 2001-344428 |
| Nov. 14, 2001 | (JP) | 2001-349145 |
| Nov. 21, 2001 | (JP) | 2001-356555 |
| Nov. 21, 2001 | (JP) | 2001-356573 |
| Nov. 29, 2001 | (JP) | 2001-364253 |
| Dec. 4, 2001 | (JP) | 2001-369808 |
| Dec. 5, 2001 | (JP) | 2001-371232 |
| Dec. 6, 2001 | (JP) | 2001-372383 |

(51) Int. Cl.
*B01J 23/00* (2006.01)
*B01J 23/10* (2006.01)
*B01J 23/40* (2006.01)
*B01J 23/42* (2006.01)

(52) U.S. Cl. ............... 502/311; 502/305; 502/313; 502/314; 502/315; 502/316; 502/321; 502/325; 502/326

(58) Field of Classification Search ........... 502/305, 502/310, 311, 314–316; 568/479
See application file for complete search history.

(56) References Cited

U.S. PATENT DOCUMENTS

| 3,761,424 A | 9/1973 | Koberstein et al. |
| 3,764,632 A | 10/1973 | Takenaka et al. |
| 3,803,204 A | 4/1974 | Grasselli et al. |
| 3,825,502 A | 7/1974 | Takenaka et al. |
| 3,907,713 A | 9/1975 | Grasselli et al. |
| 3,998,867 A | 12/1976 | Takenaka et al. |
| 4,008,280 A | 2/1977 | Watanabe et al. |
| 4,052,462 A | 10/1977 | Sakakibara et al. |
| 4,123,453 A | 10/1978 | Grasselli et al. |
| 4,148,757 A | 4/1979 | Brazdil et al. |
| 4,166,808 A | 9/1979 | Daumas et al. |
| 4,176,234 A | 11/1979 | Grasselli et al. |
| 4,212,766 A * | 7/1980 | Brazdil et al. .............. 502/205 |
| 4,280,929 A * | 7/1981 | Shaw et al. ................ 502/215 |
| 4,374,759 A | 2/1983 | Khoobiar |
| 4,418,007 A | 11/1983 | Derrien |
| 4,421,919 A | 12/1983 | Jinbo et al. |
| 4,537,874 A | 8/1985 | Sato et al. |
| 4,732,884 A * | 3/1988 | Sarumaru et al. ........... 502/205 |
| 4,803,190 A | 2/1989 | Sarumaru et al. |
| 4,837,360 A | 6/1989 | Kadowaki et al. |
| 5,072,052 A | 12/1991 | Boeck et al. |
| 5,132,269 A | 7/1992 | Sasaki et al. |
| 2002/0115008 A1* | 8/2002 | Suzuki et al. ............. 430/108.7 |
| 2005/0033093 A1* | 2/2005 | Teshigahara et al. ........ 568/479 |

FOREIGN PATENT DOCUMENTS

| CA | 1004232 | 1/1977 |
| CN | 87102247 | 12/1987 |
| CN | 1050181 | 3/1991 |
| CN | 1061166 | 5/1992 |
| EP | 0 239 071 | 9/1987 |
| EP | 0 267 556 | 5/1988 |
| GB | 1 365 580 | 9/1974 |
| JP | 39-3670 | 4/1964 |
| JP | 47-21081 | 6/1972 |
| JP | 48-503 | 1/1973 |
| JP | 48-514 | 1/1973 |
| JP | 48-1645 | 1/1973 |
| JP | 48-4763 | 2/1973 |

(Continued)

OTHER PUBLICATIONS

Notice of Grounds for Rejection drafted on Nov. 2, 2007 for Patent Application No. JP 2001-372383 and English Language translation thereof.

(Continued)

*Primary Examiner*—Jerry Lorengo
*Assistant Examiner*—Jennifer A Smith
(74) *Attorney, Agent, or Firm*—Wenderoth, Lind & Ponack, L.L.P.

(57) ABSTRACT

A composite oxide catalyst for the oxidation of an olefin containing Mo and Bi as essential components, characterized in that it has a specific surface area of 5 to 25 $m^2/g$ and a pore volume of 0.2 to 0.7 cc/g, and has a pore diameter distribution wherein the volume of the pores having a pore diameter of 0.03 to 0.1 μm accounts for 30% or more of the total pore volume, the volume of the pores having a pore diameter of 0.1 to 1 μm accounts for 20% or more of the total pore volume, and the volume of the pores having a pore diameter of less than 0.03 μm is 10% or less of the total pore volume; a composite oxide catalyst for use in the vapor phase catalytic oxidation of acrolein or methacrolein or the like which comprises Mo, Bi and a halogen; either of the above two composite oxide catalysts which comprises Mo, Bi, Fe, Si and an element selected from alkali metals and thallium, and optionally Co, Ni, Mg, Ca, Zn, Ce, Sm, a halogen, B, P, As and W; a method for preparing any of the above composite catalysts; and a method for using any of the above composite oxide catalysts.

15 Claims, No Drawings

FOREIGN PATENT DOCUMENTS

| | | |
|---|---|---|
| JP | 45-26690 | 4/1973 |
| JP | 48-17253 | 5/1973 |
| JP | 48-52713 | 7/1973 |
| JP | 48-54027 | 7/1973 |
| JP | 48-57916 | 8/1973 |
| JP | 49-3498 | 1/1974 |
| JP | 49-106985 | 10/1974 |
| JP | 52-10434 | 3/1977 |
| JP | 53-5632 | 3/1978 |
| JP | 55-13187 | 1/1980 |
| JP | 55-20610 | 2/1980 |
| JP | 55-47144 | 4/1980 |
| JP | 55-84541 | 6/1980 |
| JP | 55-36384 | 9/1980 |
| JP | 55-113730 | 9/1980 |
| JP | 55-41213 | 10/1980 |
| JP | 56-14659 | 4/1981 |
| JP | 56-23969 | 6/1981 |
| JP | 56-24658 | 6/1981 |
| JP | 56-28180 | 6/1981 |
| JP | 56-52013 | 12/1981 |
| JP | 57-26245 | 6/1982 |
| JP | 57-119837 | 7/1982 |
| JP | 57-127445 | 8/1982 |
| JP | 58-29139 | 6/1983 |
| JP | 58-113141 | 7/1983 |
| JP | 58-143843 | 8/1983 |
| JP | 59-76541 | 5/1984 |
| JP | 60028824 A * | 2/1985 |
| JP | 60-122041 | 6/1985 |
| JP | 62-213846 | 9/1987 |
| JP | 62-234548 | 10/1987 |
| JP | 62-234549 | 10/1987 |
| JP | 63-54941 | 3/1988 |
| JP | 63-54942 | 3/1988 |
| JP | 2-227140 | 9/1990 |
| JP | 03109345 A * | 5/1991 |
| JP | 03109946 A * | 5/1991 |
| JP | 4-118051 | 4/1992 |
| JP | 5-87300 | 12/1993 |
| JP | 6-13096 | 2/1994 |
| JP | 6-13097 | 2/1994 |
| JP | 7-89726 | 4/1995 |
| JP | 7-124473 | 5/1995 |
| JP | 7-289902 | 11/1995 |
| JP | 11-179206 | 7/1999 |
| JP | 2001-096162 | 4/2001 |
| JP | 2001-164239 | 6/2001 |
| JP | 2002-502699 | 1/2002 |
| WO | 99/41012 | 8/1999 |

OTHER PUBLICATIONS

Notice of Grounds for Rejection drafted Jan. 23, 2008 for Patent Application No. JP 2002-333883 and English language translation thereof.

Notice of Grounds for Rejection drafted on Mar. 4, 2008 for Patent Application No. JP 2002-330930 and English translation thereof.

English abstract of JP 63-122642 published May 26, 1988.

* cited by examiner

COMPOSITE OXIDE CATALYST AND METHOD FOR PREPARATION THEREOF

TECHNICAL FIELD

This invention relates to a composite oxide catalyst used for selective reactions such as a vapor phase catalytic oxidation reaction for producing acrolein or methacrolein from propylene, isobutene or tertiary butanol, a vapor phase contact ammoxidation reaction for producing acrylonitrile or methacrylonitrile from propylene or isobutene, and a vapor phase catalytic oxidation type dehydrogenation reaction for producing butadiene from butene, and a process for producing the same.

PRIOR ART

In selective reactions such as a vapor phase catalytic oxidation reaction for producing acrolein or methacrolein from propylene, isobutene or tertiary butanol, a vapor phase contact ammoxidation reaction for producing acrylonitrile or methacrylonitrile from propylene or isobutene, and a vapor phase catalytic oxidation type dehydrogenation reaction for producing butadiene from butene, it is well known that Mo-Bi composite oxide catalysts are useful, and they are industrially used widely.

The following patent documents disclose compositions of and methods for producing Mo—Bi composite oxides used in reactions as described above: JP patent publications 39-3670, 48-1645, 48-4763, 48-17253, 49-3498, 55-41213, 56-14659, 56-23969, 56-52013, 57-26245, 48-503, 48-514, 48-52713, 48-54027, 48-57916, 55-20610, 55-47144, 55-84541, 59-76541 and 60-122041.

Among them, except that JP patent publications 55-47144 and 59-76541 disclose producing Mo—Bi or W—Bi beforehand in producing composite oxide catalysts, any of the others uses bismuth nitrate as its raw material in Examples, and in the respective descriptions, water-soluble bismuth compounds, namely bismuth nitrate or hydroxides are recommended as Bi raw materials. While the catalysts described therein are considered to be reasonable formulas in view of uniform dispersion of Bi in composite oxide catalysts, no sufficient catalytic performance has been obtained.

Further, any of the catalysts described therein contains silicon as their component or as a carrier. Silicon is usually supplied from such a compound as silica sol or silica gel.

In JP patent publication 11-179206, in order to modify a silica as a raw material before being added, a silica sol having a pH not more than 5 is added to a slurry, and the slurry is prepared in acidic condition.

In JP patent publications 49-3498, 48-503, 48-514, etc., catalysts containing fumed silica as silicon raw material are disclosed. Fumed silica is particulate anhydrous silica produced by reacting a volatile compound containing silica in a vapor phase, and has different properties from silica gel, white carbon or a substance produced by hydrolysis of sodium silicate.

In these conventional techniques, silica sol, silica gel or fumed silica is added partly for the purpose of more effectively utilizing catalyst activating components. This object is at least partly fulfilled in these prior arrangements.

But catalysts using silica sol, silica gel, or fumed silica are still insufficient in view of the yield, and further improvement in the catalytic performance is desired.

In JP patent publication 5-87300, a composite oxide catalyst in which bismuth subcarbonate containing Na in the form of a solid solution is used as a Bi raw material is disclosed. In JP patent publication 6-13096, a composite oxide catalyst in which bismuth subcarbonate containing one of Mg, Ca, Zn, Ce and Sm in the form of a solid solution is used as a Bi raw material is disclosed. In JP patent publication 6-13097, a composite oxide catalyst in which bismuth subcarbonate containing one of Mg, Ca, Zn, Ce and Sm and Na in the form of a solid solution is used as a Bi raw material is disclosed.

As described, various catalysts have been proposed to manufacture acrolein (and also acrylic acid as an effective component) by contact vapor phase oxidation reaction of propylene with high yield. They mainly relate to the selection of components forming the catalyst and their ratios. But some of them relate to the selection of the physical properties of the catalyst or its reproducible producing method.

For the latter in particular, for composite oxide catalysts containing molybdenum (Mo), bismuth (Bi) and iron (Fe), which are used for oxidation of olefins and ammoxidation reaction too, while there are not a few proposals about catalytic physical properties such as surface areas, pore volumes and pore diameters, proposals that are at a satisfactory level have not yet been found.

For example, proposals concerning surface areas are described in JP patent publications 47-21081, 52-10434, 53-5632, 55-36382, 56-24658, 56-28180, 58-29139, and 48-26690, where surface areas in the range of 1-50 $m^2/g$ are used. But while surface areas are specified in these publications, some of them are low in activity in spite of high reaction temperature, and some are low in the selectivity of acrolein, so that they are not necessarily satisfactory as industrially feasible catalysts.

Among proposals concerning pore volumes, there is one disclosed in JP patent publication 57-119837, in which there is a description that 0.2-0.4 cc/g is preferable as the pore volume. But examples thereof concern ammoxidation.

As for pore diameters, in JP patent publication 57-119837, there is a disclosure that the average pore radius is preferably not less than 2000 angstroms, and in JP 58-113141, there is a disclosure that pores having diameters smaller than 100 angstroms have to be less than 3%. But any of the catalysts disclosed in these publications is low in activity and does not have performance as an industrial catalyst for producing acrolein and acrylic acid by the oxidation of propylene with high yield.

For catalysts used in these reactions, as high catalytic performance as possible is required in view of effective use of oil resources and rationalization of the steps in the above reactions. That is, if the raw material conversion or the selectivity improves by 0.1%, the amount of products obtained will increase on the order of several hundred to several thousand tons. Thus, improvement in the catalytic performance such as the raw material conversion or the selectivity markedly contributes to effective use of oil resources or rationalization of the steps even if it is a small improvement.

OBJECT OF THE INVENTION

Therefore, an object of this invention is to improve the catalytic performance, such as the raw material conversion and the selectivity, of a catalyst used in selective reaction such as vapor phase catalytic oxidation reaction for producing acrolein or methacrolein from propylene, isobutene or tertiary butanol, vapor phase contact ammoxidation reaction for producing acrylonitrile or methacrylonitrile from propylene or isobutene, and vapor phase catalytic oxidation type dehydrogenation reaction for producing butadiene from butene.

STRUCTURE OF THE INVENTION

Below, details of this invention are described.

Molybdenum (Mo), bismuth (Bi), silicon (Si), cobalt (Co), nickel (Ni), iron (Fe), magnesium (Mg), calcium (Ca), zinc (Zn), cerium (Ce), samarium (Sm), sodium (Na), potassium (K), rubidium (Rb), cesium (Cs), thallium (Ti), boron (B), phosphorus (P), arsenic (As), tungsten (W), fluorine (F), chlorine (Cl), bromine (Br) and iodine (I) are sometimes indicated using the element symbols in the brackets.

<Specific Surface Area, Pore Volume and Pore Diameter Distribution of Catalysts>

First, the inventors of the present application have found out that the catalyst physical properties are determined not by its surface area only, its pore volume only or its pore diameter distribution only, but that in the case of a composite oxide catalyst for olefin oxidation containing molybdenum and bismuth, particularly a catalyst for producing acrolein and acrylic acid by oxidizing propylene, a catalyst which is high in activity and superior in selectivity of the amount produced of the target substance is obtainable by comprehensively determining the specific surface area, pore volume and pore diameter distribution of the catalyst.

That is, in a composite oxide catalyst for olefin oxidation containing molybdenum and bismuth as essential components, particularly one for producing acrolein and acrylic acid by oxidizing propylene, if its specific surface area is 5-25 $m^2/g$, its pore volume is 0.2-0.7 cc/g and for the pore diameter distribution, the pore volume of the pores of which the diameters are 0.03-0.1 micrometers is not less than 30%, preferably 45-80%, of the entire pore volume, and further, the pore volume of the pores of which the diameters are 0.1-1 micrometers is not less than 20%, preferably 25-60%, of the entire pore volume, the activity and selectivity of the catalyst improve. Normally, while pores having smaller diameters contribute greatly to the specific surface area and the pore volume, in order for them to contribute to the activity and the selectivity for effective reaction products, only pores having small diameters are not enough. Only if pores having diameters in the range of 0.1-1 micrometer coexist, the catalytic performance improves.

The specific surface area used here is a surface area of a catalyst per unit weight which is measured by BET method using nitrogen absorption. The pore volume and pore diameter distribution are the pore diameter, pore volume and its distribution as measured with a porosimeter using a mercury charging method.

<Introduction of Halogen>

The composite oxide catalyst of this invention contains Mo, Bi and halogens as component elements.

While it is not known how such halogens function during the producing steps of the composite oxide catalyst, or how it exists, from the facts that they reveal their effects when the amount of halogens introduced is in a predetermined ratio with respect to Bi, that the amount of the remaining halogens is very small, and that the catalytic performance does not depend on the amount of the remaining halogens, during the heating step carried out when producing the composite oxide catalyst, the halogens presumably contribute to the promotion of heat diffusion when producing bismuth molybdate crystals, which are formed from Mo and Bi, which increases lattice deficiency of oxygen in the bismuth molybdate crystals, thereby improving the catalytic performance, particularly the raw material conversion.

As such halogens, F, Cl, Br and I can be cited. Among them, Cl is effective.

The content of halogens in the composite oxide catalyst is preferably 0.0005-0.5 atomic weight with respect to 12 atomic weight of Mo, more preferably 0.0005-0.05 in atomic weight. If its atomic weight is over 0.5, the catalytic performance may decrease. On the other hand, while it may be less than 0.0005 atomic weight, the atomic weight of 0.0005 is the measurement limit in the combustion absorption ion chromatography for measuring halogen amounts, and lesser amounts are not measurable, so that it is impossible to confirm the existence of halogens.

Also, for the amount of halogens used during preparation of the composite oxide catalyst, since not the entire amount used remains in the composite oxide catalyst, it is necessary to use a larger amount of them. Specifically, it is preferably 25-50000 ppm, more preferably 50-5000 ppm, further preferably 100-1000 ppm, with respect to Bi. If it is less than 25 ppm, the effect of introducing halogens may not appear sufficiently. On the other hand, if it is over 50000 ppm, deterioration in catalytic performance may result. The amount introduced is measured with Bi as a reference because, as will be described later, introduction of halogens is carried out using bismuth subcarbonate powder containing Bi and halogens, so that preparation is easier if Bi is used as a reference.

For the composite oxide catalyst, as component elements, it is possible to use one or two or more selected from Na, Mg, Ca, Zn, Ce and Sm.

It is presumed that if $(BiO)^+$ ions in the bismuth molybdate crystals produced in the composite oxide catalyst are replaced by $Na^+$ ions, Na increases the lattice deficiency of oxygen. Like Na, elements such as Mg, Ca, Zn and Sm that are selected in view of ion radii are also considered to increase the lattice deficiency of oxygen in the bismuth molybdate crystals. In either case, it is presumed that improvement particularly in the raw material conversion results from lattice deficiency.

The content of Na in the composite oxide catalyst is preferably 0-1 atomic weight, more preferably 0.01-1 atomic weight, with respect to 12 atomic weight of Mo. If it is more than 1 atomic weight, catalytic performance may be down. If the addition amount is less than 0.01 atomic weight, the effect of improvement in the catalytic performance due to addition of Na may be insufficient.

The content of one or more than one component element in the composite oxidation catalyst that is selected from among Mg, Ca, Zn, Ce and Sm is preferably 0-2 atomic weight, more preferably 0.01-1 atomic weight, with respect to 12 atomic weight of Mo. If it is more than 2 atomic weight, the catalytic performance may drop. If it is less than 0.01 atomic weight, the effect of improvement in the catalytic performance due to addition of the above component elements may be insufficient.

In order to further improve the selectivity in the respective reactions of the composite oxide catalyst, besides the above component elements, other atoms such as K, Rb, Cs and Tl are preferably added. They presumably improve the selectivity by existing at the boundaries or surfaces of compounds forming the composite oxide catalyst.

<General Formula of the Catalyst>

The composite oxide catalyst of this invention is expressed by the following general formula:

$MO_aBi_bCo_cNi_dFe_eX_fY_gZ_hSi_iO_j$ (wherein X is at least one kind of element selected from the group consisting of magnesium (Mg), calcium (Ca), zinc (Zn), cerium (Ce), samarium (Sm) and halogens, Y is at least one kind of element selected from the group consisting of sodium (Na), potassium (K), rubidium (Rb), cesium (Cs) and thallium (Tl), and Z is at least one kind of element selected from the group consisting of boron (B), phosphorus (P), arsenic (As) and tungsten (W). The letters a-j indicate atomic ratios of the respective elements, and when a=12, then b=0.5-7, c=0-10, d=0-10 (where c+d=1-10), e=0.05-3, f=0-2, g=0.04-2, h=0-3 and i=5-48. The letter j is a numerical value that satisfies the oxidation state of other elements.)

<Process for Producing the Catalyst>

The composite oxide catalyst having the specific properties of this invention is a compound containing the component elements forming the composite oxide catalyst, and can be produced by dissolving or dispersing compounds which can be made into an aqueous solution or suspension (hereinafter referred to as "supply source compounds for the component elements") into water and drying, molding and calcining them.

Also, the composite oxide catalyst having the specific properties of this invention can be produced by producing a catalyst precursor powder by heating a dried product obtained by drying a raw material salt aqueous solution containing as its part at least one of molybdenum, iron, nickel and cobalt and silica, then mixing the catalyst precursor powder and a bismuth compound together with a water-soluble solvent, and drying, forming and calcining it.

In the steps of producing the composite oxide catalyst according to this invention, there are no particular limitations except that as a supply source compound for the silicon component, heat-decomposed silica (fumed silica) is used, and as a supply source compound for the bismuth component, (1) one of bismuth oxide and bismuth subcarbonate, (2) bismuth subcarbonate containing at least part of predetermined Na in the form of a solid solution, (3) a composite carbonate compound of Bi and X which contains at least part of the components, or (4) a composite carbonate compound of Bi, Na and X which contains at least part of predetermined Na and X components are combined.

Specific examples of the producing process for the composite oxide catalyst according to this invention are shown below.

First, to a suitable molybdenum compound, preferably an aqueous solution of ammonium molybdate, compounds of iron, cobalt and nickel, preferably aqueous solutions of their nitrates are added. Next, compounds of sodium, potassium, rubidium, thallium, boron, phosphorus, arsenic, tungsten, etc., preferably their water-soluble salts are added in the form of aqueous solutions. Further, fumed silica is added. As the fumed silica, it is particularly preferable to use ultra-particulate anhydrous silica which is produced by hydrolyzing silanes such as silicon tetrachloride in oxygen-hydrogen flames and has an average primary particle diameter of 20-50 nm.

Next, bismuth powder is added. As described above, the bismuth powder is (1) at least one of bismuth oxide and bismuth subcarbonate, (2) bismuth subcarbonate containing at least part of predetermined Na in the form of a solid solution, (3) a composite carbonate compound of Bi and X which contains at least part of the components, or (4) a composite carbonate compound of Bi, Na and X which contains at least part of predetermined Na and X components. The bismuth supply source compound is a water-insoluble bismuth. This compound is preferably used in the form of powder. While the compounds as the raw materials for producing the catalyst may have a larger particle diameter than powder, in view of the heating step in which thermal diffusion is to be carried out, they are preferably small particles. Thus, if the compounds as the raw materials do not have small particle diameters, they should be pulverized before the heating step.

Thereafter, and after sufficiently agitating the slurry obtained, it is dried. Next, the dried granular or cake-like one is subjected to heat treatment for a short time in the temperature range of 250-350° C. in the air. At this time, in the heat-treated product obtained, while the iron, cobalt and nickel have already formed salts with acidic oxides, most of the bismuth compounds are still in the form of raw materials. This fact shows that the timing of addition of the bismuth compounds is arbitrary.

By forming the heat-treated product thus obtained into a desired shape in the above-described process, and carrying out final heat treatment for 1-16 hours preferably at a temperature of 450-650° C., a composite oxide catalyst is obtained.

The raw material salt water solution is an aqueous solution, slurry or cake containing as catalytic components molybdenum, iron, at least one of nickel and cobalt, and silica. Preparation of the raw material salt water solution is generally carried out by integrating the supply source compounds of the respective component elements in aqueous solution.

Manufacture of the composite oxide catalyst comprises the steps of integrating the supply source compounds of the respective component elements in aqueous solution and heating it.

Integration of the supply source compounds of the respective component elements in aqueous solution means that aqueous solutions or dispersions of the supply source compounds of the respective component elements are mixed or aged all at once or stepwise. That is to say, (a) a process in which the respective supply source compounds are mixed all at once, (b) a process in which the respective supply source compounds are mixed all at once and then aged, (c) a process in which the respective supply source compounds are mixed stepwise, (d) a process in which stepwise mixing and aging of the respective supply source compounds are repeated, and a combination of (a)-(d) are all included in the concept of integration of the supply source compounds for the respective component compounds. Aging is "an operation for achieving acquisition, rise of the necessary physical properties and chemical properties or progression of a predetermined reaction by treating industrial raw materials or half-finished products under specific conditions including a predetermined time and temperature" (Chemical Dictionary/Kyoritsu Shuppan). In this invention, the predetermined time is in the range of 10 minutes to 24 hours. The predetermined temperature is in the range between room temperature and the boiling point of the aqueous solutions or dispersions.

Further, such integration does not mean to carry out the above treatments only for the supply source compounds for the respective elements, but also the treatment for carrier materials that may be used as necessary, such as alumina, silica/alumina and fire-resistant oxides.

The above-mentioned heating is a heat treatment for forming oxides and composite oxides of the individual supply source compounds for the respective component elements, for forming oxides and composite oxides of composite compounds produced by the incorporation, or for forming final composite oxides produced. Heating is not necessarily carried out only once. That is, the heating may be carried out at every incorporation step shown in (a)-(d), and may also be carried out additionally after incorporation. The heating temperature is normally in the range of 200-700° C.

In the incorporation and the heating, besides them, for example, drying, pulverization and forming may be carried out before, after or between them.

In many cases, the thus obtained powder or the like is formed into desired shapes as catalyst products by a molding process such as extrusion, tableting or pelletizing. During molding, inorganic fibers such as glass fiber or various whiskers, which are generally known to have an effect of improving the strength and the degree of powdering of the catalyst, may be added. In order to control the physical properties of the catalyst with good reproducibility, additives generally known as powder binders such as ammonium nitrate, cellulose, starch, polyvinyl alcohol and stearic acid may be used.

A supply source compound for the respective elements when producing the composite oxide catalyst does not refer only to the compound for each element but may be a compound containing a plurality of elements (such as ammonium phosphomolybdate containing Mo and P).

A Mo-containing compound used to produce such an Mo/Si incorporated dispersion is not specifically limited so long as it contains Mo. For example, ammonium paramolybdate, molybdenum trioxide, molybdic acid, ammonium phosphomolybdate, phosphomolybdic acid or the like which are used as supply source compounds for Mo can be cited.

Among these supply source compounds for Mo, by using the above Mo/Si incorporated dispersion at least as a part thereof, catalytic performance of the composite oxide catalyst obtained further improves.

The supply source compound for Si may be a compound which can be dispersed to not more than 10 micrometers by the above dispersion treatment. For example, silica, colloidal silica, fumed silica, etc. can be cited. Among them, colloidal silica, which is high in aqueous dispersibility, is preferable, and fumed silica, which makes it possible to obtain high selectivity, is further preferable. These Si supply source compounds may be used in the form of powder, powder granules or slurry dispersed in liquid. If they disperse to not more than 10 micrometers in the dispersing treatment into the aqueous suspension, their shapes are not limited. That is, they may be masses, granules, powder or slurry.

Fumed silica refers to ultra-fine particulate anhydrous silica, which is produced by hydrolyzing a silane such as silicon tetrachloride in flames of oxygen and hydrogen. Unlike silica produced by a wet process, primary particles of fumed silica, which have been exposed to high temperature in vapor phase, have only outer surfaces. This is considered to be extremely effective in good selectivity in the high raw material conversion.

If such fumed silica is used, its content is preferably 40-100 wt %, more preferably 60-100 wt %, of the entire Si-containing compounds. If it is less than 40 wt %, the effect of improvement in the selectivity by the addition of fumed silica may not be obtained sufficiently.

Such fumed silica is preferably used in a dispersed state by applying dispersion treatment to agglomerated particles in an aqueous dispersion medium beforehand, i.e. in the form of a fumed silica dispersion. The primary particles of such fumed silica are in a strongly agglomerated state, so that if they are suspended in water with a generally used agitating blade, they form agglomerated particles even in the dispersion medium. In the measurement by the present inventors, when the primary particles of fumed silica having an average particle diameter of 7-50 nm was suspended in ion exchange water with an agitating blade, the average particle diameter of the agglomerated particles in the water was in the range of 10-55 micrometers. These agglomerated particles are used after pulverized to 5 micrometers or less by subjecting them to dispersion treatment. This, we presume, causes the catalytic components mixed together with the Si components to be dispersed finely, so that the raw material conversion dramatically improves.

As a method of dispersing agglomerated particles of fumed silica in an aqueous dispersion medium, any of the principles of flow of the medium, collision, pressure difference and ultrasonic waves may be used. For example, a dispersion method using a rotating shear flow produced by a homogenizer, a homomixer, a high-shear blender, etc. can be cited. A dispersion method using an orifice shrunk flow may also be cited. A dispersion method using ultrasonic waves may also be cited.

The dispersion time is not particularly limited if it is sufficient for the agglomerated particles in the aqueous dispersion medium to be pulverized to an average particle diameter of 0.1-5 micrometers. The dispersion treatment may be repeated a plurality of times.

The average particle diameter of the agglomerated particles of fumed silica in an aqueous dispersion medium after having been subjected to dispersion treatment is preferably 0.1-5 micrometers, more preferably 0.15-3 micrometers, further preferably 0.15-1 micrometer, still more preferably 0.15-0.5 micrometer. If it is greater than 5 micrometers, a sufficient raw material conversion may not be obtainable. On the other hand, even if it is less than 0.1 micrometer, it is considered to be advantageous in the catalytic performance. But this is technically difficult and no one has achieved it yet. The average particle diameter of the agglomerated particles of fumed silica in the aqueous dispersion medium was measured by a laser diffraction type particle diameter distribution measuring method according to the method described in JIS K 1150. As the measuring instrument, LMS-24 made by Seishin Enterprise was used. The average particle diameter was 50% diameter with respect to the volume.

The physical properties of the fumed silica are not particularly limited. But the average diameter of the primary particles is preferably 15-50 nm, more preferably 20-50 nm. While the average diameter may be greater than 50 nm, such particles are generally difficult to manufacture, and difficult to obtain. On the other hand, if it is smaller than 15 nm, the viscosity of the aqueous suspension will increase, so that operation may be difficult. The average diameter of the primary particles of fumed silica is the average value of diameters of 1000-10000 primary particles as measured on an electron microscopic photo.

As the aqueous medium used for dispersion of fumed silica in this invention, ion exchange water, distilled water or the like is used. In order to stabilize a finely dispersed state of the fumed silica, various kinds of stabilizers may be added. In view of nonexistence of impurities, simple steps and economical advantages, ion exchange water or distilled water is preferably used as it is.

The silica concentration in the suspension or dispersion of the fumed silica is preferably 0.1-60 wt %, more preferably 1-45 wt %, further preferably 10-30 wt %. If it is less than 0.1 wt %, the content of water added as a dispersion medium will be excessive, so that this may be economically disadvantageous in the drying step. On the other hand, if it is greater than 60 wt %, the fluidity of the dispersion will worsen extremely. Thus, there are cases in which mixing with other catalyst components is difficult.

The chemical properties of the fumed silica are not particularly limited. But since it is used in an aqueous solution, one that is not hydrophobic is suitable.

The mixing molar ratio of the Mo-containing compound and the Si-containing compound when carrying out incorporation of the Mo-containing compound and the Si-containing compound in an aqueous soloution is preferably (molar number of Mo contained)/(molar number of Si contained)=0.001-100, more preferably 0.02-24. If it is smaller than 0.001, the amount of Mo supplied as an incorporated substance obtained from the Mo-containing compound and the Si-containing compound in the composite oxide catalyst will be so small that there may be cases in which no sufficient catalytic performance is obtained. On the other hand, if it is greater than 100, the amount of Mo that is not incorporated with the Si-containing compound will be so large that it will become difficult to obtain sufficient effects by this invention.

In this invention, while it is not apparent how improved catalytic performance reveals, since an aqueous dispersion in which the Mo-containing compound and the Si-containing compound are incorporated in an aqueous solution is used, Mo is retained in the Si-containing compound first. When the supply source compounds for respective component elements other than Mo and Si, such as Co, Ni, Fe, etc. are added thereto, Mo retained by Si is gradually released, so that a precursor of a composite oxide comprising Mo and component elements other than Mo and Si, such as Co, Ni and Fe is formed uniformly. And in forming a composite oxide catalyst by carrying out incorporation in an aqueous solution and heating, the homogenized precursor also forms a composite oxide as a constituent component of the catalyst. This is considered to contribute to improvement in the catalytic performance such as the raw material conversion and the selectivity.

As the composite oxide, a composite oxide containing molybdenum, i.e. a composite oxide of molybdenum and various metals of component elements other than Mo and Si can be cited. As specific examples, an Mo—Bi composite oxide, Mo—Co composite oxide, Mo—Ni composite oxide, Mo—Fe composite oxide, Mo—Mg composite oxide, Mo—Ca composite oxide, Mo—Zn composite oxide, Mo—Ce composite oxide, Mo—Sm composite oxide, Mo—Na composite oxide, Mo—K composite oxide, Mo—Rb composite oxide, Mo—Cs composite oxide, Mo—Tl composite oxide, Mo—B composite oxide, Mo—P composite oxide, Mo—As composite oxide, Mo—W composite oxide, etc. can be cited.

This composite oxide catalyst is produced by the steps including incorporation and heating in an aqueous solution of supply source compounds of the respective component elements forming the composite oxide catalyst.

As the supply source compounds, the following can be cited as specific examples.

If Bi is used as the component element, as its supply source compound, bismuth nitrate, bismuth oxide, bismuth subcarbonate, or the like may be used.

It may be supplied as bismuth subcarbonate which contains Na or X component (at least one kind of element selected from the group consisting of Mg, Ca, Zn, Ce and Sm) in the form of solid solution. Bismuth subcarbonate which contains Na in the form of solid solution can be produced by dripping and mixing an aqueous solution of a water-soluble bismuth compound such as bismuth nitrate into e.g. an aqueous solution of sodium carbonate or sodium bicarbonate, and rinsing and drying the obtained precipitate. Bismuth subcarbonate which contains X component in the form of solid solution can be produced by dripping and mixing an aqueous solution comprising water-soluble compounds such as bismuth nitrate and a nitrate of X component into e.g. an aqueous solution of ammonium carbonate or ammonium bicarbonate, and rinsing and drying the obtained precipitate. If sodium carbonate or sodium bicarbonate is used instead of ammonium carbonate or ammonium bicarbonate, it is possible to produce bismuth subcarbonate which contains Na and X component in the form of solid solution.

The Bi or the composite carbonate compound of Bi and Na is preferably used in the form of powder. These compounds as raw materials for producing catalysts may be particles larger than powder. But in view of the heating step for thermal diffusion, they are preferably smaller particles. Thus, if the composite carbonate compound of Bi and Na is not powder, it is desirably subjected to pulverizing treatment before the heating step.

Further, if Na is used as a component element, as its supply source compound, sodium nitrate or borax may be used. It is also possible to supply it in the form of solid solution contained in bismuth subcarbonate. If a composite carbonate compound of Bi and Na is used, it is possible to further improve the catalytic performance of the composite oxide catalyst obtained.

If Fe is used as a component element, as its supply source compound, ferric nitrate, ferric sulfate, ferric chloride, ferric acetate or the like may be used. If Co is used as a component element, as its supply source compound, cobalt nitrate, cobalt sulfate, cobalt chloride, cobalt carbonate, nickel acetate or the like can be cited. If Ni is used as a component element, as its supply source compound, nickel nitrate, nickel sulfate, nickel chloride, nickel carbonate, nickel acetate or the like can be cited.

If X component (at least one kind of element selected from the group consisting of Mg, Ca, Zn, Ce and Sm) is used as a component element, as its supply source compound, a nitrate compound, sulfate compound, chloride, carbonate compound or acetate compounds of these elements can be cited. As described above, it may be supplied in the form of solid solution contained in bismuth subcarbonate.

If K is used as a component element, as its supply source compound, potassium nitrate, potassium sulfate, potassium chloride, potassium carbonate, potassium acetate or the like can be cited. If Rb is used as a component element, as its supply source compound, rubidium nitrate, rubidium sulfate, rubidium chloride, rubidium carbonate, rubidium acetate or the like can be cited. If Cs is used as a component element, as its supply source compound, cesium nitrate, cesium sulfate, cesium chloride, cesium carbonate, cesium acetate or the like may be used. If Tl is used as a component element, as its supply source compound, thallous nitrate, thallous chloride, thallium carbonate, thallous acetate or the like can be cited.

If B is used as a component element, as its supply source compound, borax, ammonium borate, boric acid or the like can be cited. If P is used as a component element, as its supply source compound, ammonium phosphomolybdate, ammonium phosphate, phosphoric acid, phosphorus pentoxide or the like can be cited. If As is used as a component element, as its supply source compound, diarceno 18 ammonium molybdate, diarceno 18 ammonium tungstate or the like can be cited. If W is used as a component element, as its supply source compound, ammonium paratungstate, tungsten trioxide, tungstic acid, phosphotungstic acid or the like can be cited.

As a supply source compound for Si, one used in the preparation of the Mo/Si incorporated aqueous dispersion is used. But besides this aqueous dispersion, the above raw material compounds may be added.

Specific examples of the process for producing the composite oxide catalyst shown by the general formula (1) are shown below. At the time the above patent documents and others became known, it is believed that from these specific examples, other specific examples were obvious to a person of ordinary skill in the art.

First, an Mo-containing compound such as ammonium paramolybdate and an Si-containing compound such as fumed silica are incorporated in an aqueous solution to manufacture an incorporated dispersion.

With this Mo/Si incorporated dispersion as a supply source compound for Mo and Si, supply source compounds for e.g. Fe, Co, Ni, Mg, Ca, Zn, Ce, Na, K, Rb, Cs, Tl, B, P, As or W, for example, their water-soluble salts are added. And the supply source compound for Bi and the supply source compound for Na, preferably composite carbonate compounds of Bi and Na are added.

And after the suspension or slurry obtained has been agitated sufficiently, it is dried. The dried particulate or cake-like one is subjected to heat treatment for a short time in a temperature range of 250-350° C. in the air. The primary heat treated product thus obtained is formed into a desired shape by such a method as extrusion molding, tablet molding or carrier molding. Next this molded product is preferably subjected to final heat treatment under the temperature conditions of 450-650° C. for about 1-16 hours. Thus, the composite oxide catalyst according to this invention is produced.

If bismuth subcarbonate containing Na is used as a supply source compound for Bi and Na, in the primary heat-treated product obtained by the short heat treatment, while iron, cobalt and nickel had already formed salts with acidic oxides, most part of the bismuth subcarbonate containing Na still showed the form of raw materials. This means that the addition timing of the bismuth subcarbonate is not limited to before the short-time heat treatment but may be after the short-time heat treatment.

On the other hand, as for the addition timing of the Mo/Si incorporated aqueous dispersion, since it is supplied as an aqueous dispersion, the effect is exhibited by adding in the step before the short-time heat treatment.

The adding amounts of the respective supply source compounds in the above producing process may be set according to the constitution ratio of the constituent elements of the composite oxide catalyst expressed by the above general formula (1).

If the composite oxide catalyst expressed by the general formula (1) is produced by a process comprising incorporating the supply source compounds of the respective component elements into a composite in an aqueous solution and subjecting the composite to heat treatment, it is prepared by, after going through a pre-step in which a catalytic precursor is produced by heat-treating a raw material salt solution containing at least one of molybdenum equivalent to a partial atomic ratio ($a_1$) of the entire atomic ratio (a) of the molybdenum of the general formula (1), iron, nickel and cobalt, and silica, or a dried product obtained by drying it, going through an after-step in which the catalytic precursor, molybdenum equivalent to the remaining atomic ratio ($a_2$) in which the ratio $a_1$ is subtracted from the whole atomic ratio (a) of the general formula (1), and a bismuth compound are incorporated together with an aqueous solvent, dried and calcined.

The ignition loss of the catalyst precursor obtained after heat treatment is preferably 0.5-5 wt %, more preferably 1-3 wt %. By determining the ignition loss in this range, it is possible to obtain a catalyst that is high in the raw material conversion and the selectivity. The ignition loss is a value given by the following formula:

Ignition loss (%)=[($W_0-W_1$)/$W_0$]×100

$W_0$: weight (g) of the catalyst precursor after drying three hours at 150° C. to remove adhering water content $W_1$: weight (g) of the catalyst precursor after heating it another two hours at 500° C. after removing adhering water content The entire atomic ratio a of the molybdenum in the catalyst of this invention is 12, which is divided into the atomic ratios $a_1$ and $a_2$ for the pre- and after-steps and incorporated. The values of the atomic ratios $a_1$ and $a_2$ at this time are preferably in the following relation. That is, $a_1$ is a value that satisfies $1<a_1/(c+d+e)<3$, and $a_2$ is a value that satisfies $0<a_2b<8$.

Next, as supply source compounds containing Bi and halogens, as essential components, and as optional components, Na, and/or component elements consisting of one or two or more selected from Mg, Ca, Zn, Ce and Sm (hereinafter abbreviated to "supply source compounds for Bi or the like"), a composite carbonate compound of Bi containing component elements consisting of halogens as essential components, and Na and/or one or two or more selected from Mg, Ca, Zn, Ce and Sm as optional components (which are hereinafter abbreviated to "halogens") can be cited. As examples thereof, (water-insoluble) bismuth subcarbonate containing halogens or the like can be cited. This compound can be produced by dripping and mixing a water-soluble bismuth compound such as bismuth nitrate into a mixed solution of an aqueous solution of a carbonate and/or a bicarbonate such as ammonium carbonate or ammonium bicarbonate, and an aqueous solution of a water-soluble halogenated substance such as halogenated ammonium, and rinsing and drying the thus obtained precipitate.

In order for it to contain Na, an aqueous solution of sodium carbonate or sodium bicarbonate may be used as a carbonate and/or a bicarbonate, and as a halogenated substance, an aqueous solution of halogenated sodium may be used. Further, in order for it to contain one or two or more selected from Mg, Ca, Zn, Ce and Sm, an aqueous solution or the like of nitrates of these elements may be used by mixing in an aqueous solution of a water-soluble bismuth compound such as bismuth nitrate. The addition amount of Bi, Na, Mg, Ca, Zn, Ce or Sm at this time is adjusted according to the content of the composite oxide catalyst. The amount of the halogens is adjusted according to the below-described amount.

Bismuth subcarbonate containing the water-insoluble halogens or the like is preferably used in the form of powder. These compounds as raw materials for producing the catalyst may be of larger particles than powder, but in view of the heating step in which heat diffusion is carried out, they are preferably of small diameters. Thus, if these compounds as raw materials are not of small particles, they should be pulverized before the heating step.

Specific examples of the producing method of the composite oxide catalyst shown by the above general formula (1) are shown below, e.g. for the case in which Cl is used as a halogen. At the time when the above-described patent documents are known, from these specific examples, other specific examples are believed to have been obvious to a person of ordinary skill in the art.

First, to a suitable supply source compound for Mo, such as an aqueous solution of ammonium paramolybdate, a supply source compound for Fe, Co and Ni, such as an aqueous solution of their respective nitrates is added. Further, supply source compounds for Na, K, Cs, Rb, Tl, B, P, As and W, such as their respective water-soluble salts are added to this aqueous solution. Further, as necessary, a supply source compound for Si such as particulate or colloidal silica or fumed silica is added. Thus, a supply source compound aqueous solution or suspension for Mo or the like is prepared.

Next, as a composite carbonate compound of Bi containing halogens or the like, bismuth subcarbonate containing halogens or the like is prepared.

This is obtained by preparing an aqueous solution of a bismuth-containing compound, e.g. bismuth nitrate, dripping and mixing it into a mixed solution of an aqueous solution of a Cl-containing compound such as ammonium chloride and an aqueous solution of a carbonate ion or bicarbonate ion-containing compound such as ammonium carbonate or ammonium bicarbonate, and rinsing and drying the thus obtained precipitate. In order for it to contain Na as an optional component, sodium chloride may be used as a Cl-containing compound, or as a carbonate ion- or bicarbonate ion-containing compound, sodium carbonate or sodium bicarbonate may be used. In order for it to contain Mg, Ca, Zn, Ce, Sm or the like, an aqueous solution of e.g. nitrates thereof may be used by mixing with an aqueous solution of bismuth nitrate. By this preparation method, Na and Mg, Ca, Zn, Ce or Sm is contained in bismuth subcarbonate containing halogens or the like.

Next, powder of bismuth subcarbonate containing halogens or the like is mixed into an aqueous solution or suspension of the supply source compound for Mo or the like. And after sufficiently agitating the suspension or slurry obtained, it is dried. The dried granular or cake-like one is subjected to a short-time heat treatment in the air in the temperature range of 250-350° C.

The thus obtained primary heat-treated product is formed into a desired shape by extrusion molding, tablet molding or carrier molding. Next, the thus molded product is preferably subjected to final heat treatment under the temperature conditions of 450-650° C. for 1-16 hours. The composite oxide catalyst according to this invention is thus produced.

In the primary heat-treated product obtained by such short-time heat treatment, while iron, cobalt and nickel had already formed salts with acidic oxides, most part of the bismuth subcarbonate containing halogens or the like was in the form of raw material. This means that the addition timing for the bismuth subcarbonate containing halogens or the like is not limited to before the short-time heat treatment, but may be after the short-time heat treatment.

Thus, besides the method in which, as described above, comprehensive integration and short-time or long-time heat treatment are carried out, i.e. after mixing all of the supply source compounds, the mixture is heated, a method may be used in which after integrating and heating the supply source compounds other than the composite carbonate compound of Bi containing halogens or the like, the supply source compound for Si in an aqueous solution, the composite carbonate compound of Bi containing halogens or the like and the supply source compound for Si are mixed, and after molding, they are incorporated and heated. Since Si plays the role of a carrier, there will be no problem no matter in whichever stage it is added.

The addition amounts of the respective supply source compounds in the above producing method may be set according to the constituent ratio of the constituent elements of the composite oxide catalyst shown by the general formula (1).

In producing powder of bismuth subcarbonate containing halogens or the like, the addition amounts of the Bi-containing compound, Na-containing compound and a compound containing at least one kind of Mg, Ca, Zn, Ce and Sm may be set so that the amounts of Bi, Na, Mg, Ca, Zn, Ce or Sm will meet the constituent ratio of the constituent elements of the composite oxide catalyst expressed by the general formula (1). For the addition amount of the Cl-containing compound, it is necessary to introduce it in a greater amount because not all of Cl introduced remains in the composite oxide catalyst. Specifically, it is preferably added such that the Cl amount will be 25-50000 wt ppm, preferably 50-5000 wt ppm, more preferably 100-1000 wt ppm, with respect to Bi. If it is less than 25 wt ppm, when bismuth molybdate crystals are formed, it will not sufficiently contribute to the promotion of thermal diffusion, so that the lattice deficiency of oxygen in the bismuth molybdate crystals may not increase sufficiently. On the other hand, if it is greater than 50000 wt ppm, deterioration in the catalyst performance may result.

The atomic number of halogens in the composite oxide catalyst expressed by the general formula (1) in the above producing process, when Mo=12, is preferably 0-0.5, more preferably 0.0005-0.5 as described above. If the value j is greater than 0.5, the catalyst performance may decrease. On the other hand, the value j may be zero, that is, halogens may not be present in the composite oxide catalyst expressed by the general formula (1), which is obtained by the above producing process. If the value j exceeds 0 and is less than 0.0005, this is less than the measurement limit in the combustion absorption ion chromatography for measuring halogen amounts, and is judged as the value is 0. Even if the value is in the range of 0-0.0005, since halogens are added during preparation of the catalyst in the above producing process, it sufficiently contributes to the promotion of thermal diffusion when forming bismuth molybdate crystals, thus sufficiently increasing the lattice deficiency of oxygen in the bismuth molybdate crystals. Thus, in this producing process, even if the halogen amount in the composite oxide catalyst finally obtained is not more than the detection limit, the object of this invention is achieved.

The composite oxide catalyst produced in this process can be used for various vapor phase catalytic oxidation reactions carried out in the presence of molecular oxygen.

As specific examples of the vapor phase catalytic oxidation reaction mentioned here, as described above, the reaction in which acrolein or methacrolein is produced from propylene, isobutene or tertiary butanol, the reaction in which acrylonitrile or methacrylonitrile is produced from propylene or isobutene in the presence of ammonia, the reaction in which butadiene is produced from butene, etc. can be cited.

The vapor phase catalytic oxidation reaction using the composite oxide catalyst according to this invention is carried out by introducing as the raw material gas composition a mixture gas comprising 1-10 vol % of propylene, 5-18 vol % of molecular oxygen, 0-60 vol % of steam, and 20-70 vol % of inert gas such as nitrogen or carbon dioxide gas onto the catalyst prepared as described above in the temperature range of 250-450° C. under the pressure from atmospheric pressure to 10 atm for the contact period of 0.5-10 seconds.

EXPERIMENT EXAMPLES

The definitions of the propylene conversion, acrolein selectivity, acrylic acid selectivity, acrolein yield, acrylic acid yield, and total yield are as follows:

.Propylene conversion (molar %)=(molar number of the reacted propylene/molar number of the supplied propylene)×100

.Acrolein selectivity (molar %)=(molar number of the acrolein produced/molar number of the reacted propylene)×100

.Acrylic acid selectivity (molar %)=(molar number of the acrylic acid produced/molar number of the reacted propylene)×100

.Acrolein yield (molar %)=(molar number of the acrolein produced/molar number of the supplied propylene)×100

.Acrylic acid yield (molar %)=(molar number of the acrylic acid produced/molar number of the supplied propylene)×100

.Total yield (molar %)=acrolein yield (molar %)+acrylic acid yield (molar %)

<Effect confirmation experiments by physical properties such as specific surface area>

Experiment Example 1

First, 94.1 g of ammonium paramolybdate was dissolved in 400 ml of pure water under heating. Next, 7.18 g of ferric nitrate, 25.8 g of cobalt nitrate and 37.8 g of nickel nitrate were dissolved in 60 ml of pure water under heating. These solutions were gradually mixed while agitating. Next, 0.85 g of borax and 0.36 g of potassium nitrate were dissolved into 40 ml of pure water while heating, and added to the above slurry. Next, 48 g of heat-decomposed silica (fumed silica) (having an average primary particle diameter of 40 nm) was added and sufficiently agitated. Next, 58.1 g of bismuth subcarbonate which contains 0.57% Na in the form of solid solution was added and mixed by agitating. After heat drying of the slurry, it was subjected to thermal treatment at 300° C. for an hour in an aerial atmosphere. The particulate solid obtained was formed into tablets having a diameter of 5 mm and a height of 4 mm by the use of a small molding machine. Next, they were calcined at 500° C. for four hours to form a composite oxide catalyst.

The atomic ratio of the composite oxide catalyst as calculated from raw materials used was as follows:
Mo:Bi:Co:Ni:Fe:Na:B:K Si=12:5:2:3:0.4:0.39:0.2:0.08:18

Experiment Example 2

94.1 g of ammonium paramolybdate was dissolved in 400 ml of pure water under heating. Next, 7.18 g of ferric nitrate, 25.8 g of cobalt nitrate and 37.8 g of nickel nitrate were dissolved in 60 ml of pure water under heating. These solutions were gradually mixed while agitating.

Next, 0.85 g of borax and 0.36 g of potassium nitrate were dissolved into 40 ml of pure water while heating, and added to the above slurry. Next, 48 g of heat-decomposed silica (having an average primary particle diameter of 40 nm) was added and sufficiently agitated. After heat drying of the slurry, it was subjected to thermal treatment at 300° C. for an hour in an aerial atmosphere. The particulate solid obtained was pulverized and dispersed in a solution of 150 ml of pure water to which 10 ml of ammonia solution was added. Next, 58.1 g of bismuth subcarbonate which contained 0.52% of Na in the form of solid solution was added and mixed by agitating. After heat drying of the slurry, the particulate solid obtained was formed into tablets having a diameter of 5 mm and a height of 4 mm by use of a small molding machine. Next, they were calcined at 500° C. for four hours to form a catalyst.

The catalyst was a composite oxide having the following atomic ratio as calculated from the raw materials used:
Mo:Bi:Co:Ni:Fe:Na:B:K:Si=12:5:2:3:0.4:0.37:0.2:0.08:18

Experiment Example 3

54 g of ammonium paramolybdate was dissolved in 250 ml of pure water under heating. Next, 7.18 g of ferric nitrate, 25.8 g of cobalt nitrate and 37.8 g of nickel nitrate were dissolved in 60 ml of pure water under heating. These solutions were gradually mixed while agitating.

Next, 48 g of heat-decomposed silica was added and sufficiently agitated. After heating and drying the slurry, it was subjected to thermal treatment at 300° C. for an hour in an aerial atmosphere. The particulate solid obtained as a catalyst precursor (ignition loss: 1.3 wt %) was pulverized, and dispersed in a solution which 40.1 g of ammonium paramolybdate was dissolved in 150 ml of pure water adding 10 ml of an ammonia solution. Next, 0.85 g of borax and 0.36 g of potassium nitrate were dissolved into 40 ml of pure water, and added to the slurry. Next, 58.1 g of bismuth subcarbonate which contained 0.45% of Na in the form of solid solution was added and mixed by agitating.

After heat drying of the slurry, the particulate solid obtained was formed into tablets having a diameter of 5 mm and a height of 4 mm by the use of a small molding machine. Next, they were calcined at 500° C. for four hours to form a catalyst.

The catalyst was a composite oxide having the following atomic ratio as calculated from the raw materials used:
Mo:Bi:Co:Ni:Fe:Na:B:K:Si=12:5:2:3:0.4:0.35:0.2:0.08:18

The atomic ratios $a_1$ and $a_2$ of molybdenum during preparation were 6.9 and 5.1 respectively.

Comparative Experiment Example 1

Except that colloidal silica was used as the silica raw material, preparation of a composite oxide catalyst was made in the same manner as in Experiment Example 1. Table 1 shows the results of measurement of physical properties of the composite oxide catalyst obtained such as the specific surface area, and the results of oxidation reaction of propylene carried out using the composite oxide catalyst obtained.

[Comparative Experiment Example 2]

Except that in preparing a catalyst having the same composition as in Experiment Example 2, the bismuth raw material was added simultaneously with the other raw materials, and colloidal silica was used as the silica raw material, preparation was made in the same manner as in Experiment Example 2. The results of measurement of physical properties of the composite oxide catalyst obtained such as the specific surface area, and the results of oxidation reaction of propylene carried out using the composite oxide catalyst obtained are shown in Table 1.

Comparative Experiment Example 3

A catalyst having the same composition as in Experiment Example 3 was prepared as follows. 94.1 g of ammonium paramolybdate was dissolved in 400 ml of pure water under heating. Next, 7.18 g of ferric nitrate, 25.8 g of cobalt nitrate and 37.8 g of nickel nitrate were dissolved in 60 ml of pure water under heating. These solutions were gradually mixed while agitating.

Next, 0.85 g of borax and 0.36 g of potassium nitrate were dissolved into 40 ml of pure water while heating, and added to the above slurry. Next, 240 g of colloidal silica (SiO$_2$ content 20 wt %) was added and sufficiently agitated. After heat drying of the slurry, it was subjected to thermal treatment at 300° C. for an hour in an aerial atmosphere. The particulate solid obtained was pulverized and dispersed in a solution of 150 ml of pure water adding 10 ml of an ammonia solution. Next, 58.1 g of bismuth subcarbonate which contains 0.45% of Na in the form of solid solution was added and mixed by agitating. After heat drying of the slurry, the particulate solid obtained was formed into tablets having a diameter of 5 mm and a height of 4 mm by the use of a small molding machine. Next, they were calcined at 500° C. for four hours to form a catalyst. Using this composite oxide catalyst, which was produced in the same manner as in Experiment Example 3 except that the supply source of the molybdenum component was added not separately from but simultaneously with the X, Y and Z components and prepared, and that as the silica raw material, colloidal silica was used, oxidation reaction of propylene was carried out in the same manner as in Experiment Example 3. The results thereof are shown in Table 1.

(Measurement of Physical Properties of the Composite Oxide Catalyst of Experiment Examples 1-3 and Comparative Experiment Examples 1-3)

The specific surface area, pore volume and pore distribution of the composite oxide catalysts prepared as above were measured as follows. The results are shown in Table 1.

The specific surface area was measured by BET method using nitrogen absorption. As the measuring device, Type AMS-8000 made by Ohkura Riken was used.

The pore volume and pore distribution were measured by a mercury charging method. For the measuring device, Pore Sizer 9310-PC2 made by Shimadzu was used.

(Oxidation Reaction of Propylene)

Using the composite oxide catalysts prepared as above, oxidation reaction of propylene was carried out and the propylene conversion, acrolein yield and acrylic acid yield were calculated.

Oxidation reaction of propylene was carried out by charging 20 ml of composite oxide catalyst into a reaction tube with a jacket for a nitrate heating media and having an inner diameter of 15 mm and made of stainless steel, and passing a raw material gas having 10% of propylene concentration, 17% of steam concentration and 73% of air concentration under atmospheric pressure in a reaction temperature of 310° C. with the contact period at 2.0 seconds for Experiment Example 1 and Comparative Experiment Example 1, 305° C. with the contact period at 1.8 seconds for Experiment Example 2 and Comparative Experiment Example 2, and 300° C. with the contact period at 1.8 seconds for Experiment Example 3 and Comparative Experiment Example 3. The results are shown in Table 1.

In Table 1, the rate of the pore volume was the rate of the volume of the pores having diameters in the range of 0.03-0.1 μm or in the range of 0.1-1 μm relative to the entire pore volume.

and the acrolein yield and the acrylic acid yield were low compared with those of Experiment Examples 1-3.

<Effect Confirmation Experiment as to the Addition Timing of the Bi Raw Material>

Experiment Example 4

94.1 g of ammonium paramolybdate was dissolved in 400 ml of pure water under heating. Next, 7.18 g of ferric nitrate, 25.8 g of cobalt nitrate and 37.8 g of nickel nitrate were dissolved in 60 ml of pure water under heating. These solutions were gradually mixed while agitating.

Next, 0.85 g of borax and 0.36 g of potassium nitrate were dissolved into 40 ml of pure water while heating, and added to the above slurry. Next, 64 g of silica was added and sufficiently agitated. After heat drying of the slurry, it was subjected to thermal treatment at 300° C. for an hour in an aerial atmosphere. The particulate solid obtained was pulverized and dispersed in a solution of 150 ml of pure water adding 10 ml of an ammonia solution. Next, 58.1 g of bismuth subcarbonate which contained 0.45% of Na in the form of solid solution was added and mixed by agitating. After heat drying of the slurry, the particulate solid obtained was formed into tablets having a diameter of 5 mm and a height of 4 mm by the use of a small molding machine. Next, they were calcined at 500° C. for four hours to form a catalyst.

The catalyst was a composite oxide having the following atomic ratio as calculated from the raw materials used:
Mo:Bi:Co:Ni:Fe:Na:B:K:Si=12:5:2:3:0.4:0.35:0.2:0.08:24

(Oxidation Reaction of Propylene of Experiment Example 4)

Oxidation reaction of propylene was carried out by charging 20 ml of composite oxide catalyst into a reaction tube with a jacket for a nitrate heating media and having an inner diameter of 15 mm and made of stainless steel, and passing a raw material gas having 10% of propylene concentration, 17% of steam concentration and 73% of air concentration under atmospheric pressure in a reaction temperature of 310° C. with the contact period at 1.8 seconds. The results are shown in Table 2.

Comparative Experiment Example 4

Using a composite oxide catalyst having the same composition as in Experiment Example 3 and prepared in the same manner as in Experiment Example 3 except that a Bi raw material was added simultaneously with the other mate-

TABLE 1

| | Specific surface area | Pore volume | Rate of pore volume (0.03~0.1 μm) | Rate of pore volume (0.1~1 μm) | Propylene conversion | Yield of acrolein | Yield of acrylic acid |
|---|---|---|---|---|---|---|---|
| EEI* 1 | 18.8 | 0.35 | 68 | 23 | 98.2 | 90.3 | 4.5 |
| EEI* 2 | 17.7 | 0.36 | 63 | 28 | 98.0 | 90.3 | 4.3 |
| EEI* 3 | 17.0 | 0.36 | 60 | 35 | 99.0 | 90.7 | 4.6 |
| CEE** 1 | 29.0 | 0.32 | 70 | 10 | 98.1 | 88.2 | 4.1 |
| CEE** 2 | 28.9 | 0.32 | 69 | 10 | 95.5 | 86.4 | 3.3 |
| CEE** 3 | 27.5 | 0.33 | 68 | 11 | 96.5 | 87.3 | 3.4 |

*Experiment Example according to the Invention
**Comparative Experiment Example

For the composite oxide catalysts obtained in Comparative Experiment Examples 1-3, the specific surface area was excessive, the pore volume rate for 0.1-1 μm was too small, rials, oxidation reaction of propylene was carried out in the same manner as in Experiment Example 4. The results of the reaction are shown in Table 2.

TABLE 2

| | Propylene conversion | Yield of acrolein | Yield of acrylic acid |
|---|---|---|---|
| EEI* 4 | 98.5 | 90.6 | 4.5 |
| CEE** 4 | 96.6 | 88.8 | 3.8 |

*Experiment Example according to the Invention
**Comparative Experiment Example

<Effect Confirmation Experiment as to the Addition Timing of the Mo Component>

Experiment Example 5

54 g of ammonium paramolybdate was dissolved in 250 ml of pure water under heating. Next, 7.18 g of ferric nitrate, 31.8 g of cobalt nitrate and 31.8 g of nickel nitrate were dissolved in 60 ml of pure water under heating. These solutions were gradually mixed while agitating.

Next, 64 g of silica was added and sufficiently agitated. After heat drying of the slurry, it was subjected to thermal treatment at 300° C. for an hour in an aerial atmosphere. The particulate solid obtained as a catalyst precursor (ignition loss: 1.4 wt %) was pulverized, and dispersed in a solution which 40.1 g of ammonium paramolybdate was dissolved in 150 ml of pure water adding 10 ml of an ammonium solution. Next, 0.85 g of borax and 0.36 g of potassium nitrate were dissolved into 40 ml of pure water under heating, and added to the slurry. Next, 58.1 g of bismuth subcarbonate which contained 0.45% of Na in the form of solid solution was added and mixed by agitating.

After heat drying of the slurry, the particulate solid obtained was formed into tablets having a diameter of 5 mm and a height of 4 mm by the use of a small molding machine. Next, they were calcined at 500° C. for four hours to form a catalyst.

The catalyst was a composite oxide having the following atomic ratio as calculated from raw materials used:

Mo:Bi:Co:Ni:Fe:Na:B:K:Si=12:5:2.5:2.5:0.4:0.35:0.2: 0.08:24

The atomic ratios $a_1$ and $a_2$ of molybdenum during preparation were 6.9 and 5.1 respectively.

(Oxidation Reaction of Propylene of Experiment Example 5)

Oxidation reaction of propylene was carried out by charging 20 ml of composite oxide catalyst into a reaction tube with a jacket for a nitrate heating media and having an inner diameter of 15 mm and made of stainless steel, and passing a raw material gas having 10% of propylene concentration, 17% of steam concentration and 73% of air concentration under atmospheric pressure in a reaction temperature of 305° C. with the contact period at 1.8 seconds. The results are shown in Table 3.

Comparative Experiment Example 5

A catalyst having the same composition as in Experiment Example 5 was prepared as follows. 94.1 g of ammon paramolybdate was dissolved in 400 ml of pure water under heating. Next, 7.18 g of ferric nitrate, 31.8 g of cobalt nitrate and 31.8 g of nickel nitrate were dissolved in 60 ml of pure water under heating. These solutions were gradually mixed while agitating.

Next, 0.85 g of borax and 0.36 g of potassium nitrate were dissolved into 40 ml of pure water while heating, and added to the above slurry. Next, 64 g of silica was added and sufficiently agitated. After heat drying of the slurry, it was subjected to heat treatment at 300° C. for an hour in an aerial atmosphere. The particulate solid obtained was pulverized and dispersed in a solution of 150 ml of pure water adding 10 ml of an ammonia solution. Next, 58.1 g of bismuth subcarbonate which contained 0.45% of Na in the form of solid solution was added and mixed by agitating. After heat drying of the slurry, the particulate solid obtained was formed into tablets having a diameter of 5 mm and a height of 4 mm by the use of a small molding machine. Next, they were calcined at 500° C. for four hours to form a catalyst. Using this composite oxide catalyst, which was prepared in the same manner as in Experiment Example 5 except that the supply source of the molybdenum component was added not separately from but simultaneously with the X, Y and Z components and prepared, oxidation reaction of propylene was carried out in the same manner as in Experiment Example 5. The results of the reaction are shown in Table 3.

TABLE 3

| | Propylene conversion | Yield of acrolein | Yield of acrylic acid |
|---|---|---|---|
| EEI* 5 | 99.1 | 90.8 | 4.7 |
| CEE** 5 | 95.4 | 87.8 | 3.6 |

*Experiment Example according to the Invention
**Comparative Experiment Example

<Effect Confirmation Experiment as to the Addition of Halogens>

Experiment Example 6

94.1 g of ammon paramolybdate was dissolved in 400 ml of pure water under heating. Next, 7.18 g of ferric nitrate, 25.8 g of cobalt nitrate and 38.7 g of nickel nitrate were dissolved in 60 ml of pure water under heating. These two solutions were gradually mixed while agitating. Next, to this mixed solution, a solution in which 0.85 g of borax and 0.36 g of potassium nitrate were dissolved into 40 ml of pure water while heating, was added and sufficiently agitated to prepare an aqueous solution of a supply source compound for Mo or the like.

Next, 100 g of bismuth nitrate was dissolved into ion exchange water which was made acidic with nitric acid. Also, 42.0 g of sodium carbonate and 0.3 g of sodium chloride were dissolved into ion exchange water under heating. These two solutions were gradually mixed while sufficiently agitating. After mixing by agitation, the white precipitate obtained was washed, filtered and dried. The contents of Cl and Na in the bismuth subcarbonate obtained, which contained halogens or the like, were 0.18 wt % and 0.52 wt %, respectively.

Next, to an aqueous solution of the supply source compound for Mo or the like, 58.1 g of powder of the bismuth subcarbonate containing 64 g of silica were added and mixed together by agitating.

Next, after heat drying of the slurry, it was subjected to thermal treatment at 300° C. for an hour in an aerial atmosphere. The particulate solid obtained was formed into tablets having a diameter of 5 mm and a height of 4 mm by the use of a small molding machine. Next, they were calcined at 500° C. for four hours in a muffle furnace to form a composite oxide catalyst.

The composition ratios of the metal ingredients of the composite oxide catalyst as calculated from the raw materials used was as shown in Table 4. On the other hand, the Cl content in the composite oxide catalyst was measured by the following method. The atomic ratio thereof is shown in Table 4.

Oxidation reaction of propylene was carried out by charging 20 ml of composite oxide catalyst into a reaction tube with a jacket for a nitrate heating media and having an inner diameter of 15 mm and made of stainless steel, and passing a raw material gas having 10% of propylene concentration, 17% of steam concentration and 73% of air concentration under atmospheric pressure with the contact period at 2.3 seconds. At a reaction temperature of 310° C., the oxidation reaction results shown in Table 5 were obtained.

(Measurement Method of the Cl Content)

Measurement was made using combustion absorption ion chromatography. That is, a combustion improver was added to the analysis specimens, heated to 100° C. to let the gas produced absorbed into pure water, and determination was made by ion chromatography.

Comparative Experiment Example 6

100 g of bismuth nitrate was dissolved into ion exchange water which was made acidic with nitric acid. Also, 42.0 g of sodium carbonate was dissolved into ion exchange water under heating. These two solutions were gradually mixed while sufficiently agitating. After mixing by agitation, the white precipitate obtained was washed, filtered and dried. The Na content of the bismuth subcarbonate obtained was 0.53 wt %.

A composite oxide catalyst was prepared in the same manner as in Experiment Example 6 except that instead of the bismuth subcarbonate of Experiment Example 6, which contained halogens or the like, the above bismuth subcarbonate powder containing Na was used, and oxidation reaction of propylene was carried out. The composition ratios of the metal ingredients of the composite oxide catalyst, and the reaction results at the reaction temperature of 310° C. are shown in Table 5.

Experiment Example 7

100 g of bismuth nitrate and 25 g of magnesium nitrate were dissolved into ion exchange water which was made acidic with nitric acid. Also, 38.1 g of ammonium carbonate and 0.3 g of ammonium chloride were dissolved into ion exchange water under heating. These two solutions were gradually mixed while sufficiently agitating. After mixing by agitation, the white precipitate obtained was washed, filtered and dried. The Cl and Mg contents of the bismuth subcarbonate obtained, which contained halogens or the like, were 0.09 wt % and 0.83 wt %, respectively.

A composite oxide catalyst was prepared in the same manner as in Experiment Example 6 except that instead of the bismuth subcarbonate which contained the halogens or the like described in Experiment Example 6, bismuth subcarbonate containing the above halogens or the like was used, and oxidation reaction of propylene was carried out. The composition ratios of the metal ingredients of the composite oxide catalyst, and the oxidation reaction results at the reaction temperature of 310° C. are shown in Table 5.

Comparative Experiment Example 7

100 g of bismuth nitrate and 25 g of magnesium nitrate were dissolved into ion exchange water which was made acidic with nitric acid. Also, 38.1 g of ammonium carbonate was dissolved into ion exchange water under heating. These two solutions were gradually mixed while sufficiently agitating. After mixing by agitation, the white precipitate obtained was washed, filtered and dried. The Mg content of the bismuth subcarbonate obtained, which contained Mg, was 0.83 wt %.

A composite oxide catalyst was prepared in the same manner as in Experiment Example 6 except that instead of the bismuth subcarbonate which contained the halogens or the like described in Experiment Example 6, the above bismuth subcarbonate, which contained Mg, was used, and oxidation reaction of propylene was carried out. The composition ratios of the metal ingredients of the composite oxide catalyst, and the reaction results at the reaction temperature of 310° C. are shown in Table 5.

Experiment Example 8

100 g of bismuth nitrate and 25 g of calcium nitrate were dissolved into ion exchange water which was made acidic with nitric acid. Also, 42 g of sodium carbonate and 0.3 g of sodium chloride were dissolved into ion exchange water under heating. These two solutions were gradually mixed while sufficiently agitating. After mixing by agitation, the white precipitate obtained was washed, filtered and dried. The Cl, Na and Ca contents of the bismuth subcarbonate obtained, which contained halogens or the like were 0.09 wt %, 0.45 wt % and 0.30 wt %, respectively.

A composite oxide catalyst was prepared in the same manner as in Experiment Example 1 except that instead of the bismuth subcarbonate which contained the halogens or the like described in Experiment Example 6, the bismuth subcarbonate which contained the above halogens or the like was used, and oxidation reaction of propylene was carried out. The composition ratios of the metal ingredients of the composite oxide catalyst, and the oxidation reaction results at the reaction temperature of 310° C. are shown in Table 5.

Experiment Examples 9-12

Except that bismuth subcarbonate containing halogens or the like was prepared such that the kinds and amounts of metals composited in bismuth subcarbonate containing halogens and the amounts of chloride ions will be of the values shown in Table 6, the composite oxide catalysts shown in Table 4 were prepared in the same manner as in Experiment Example 6. And using these catalysts, reactions under the same conditions as in Experiment Example 6 were carried out. Composition ratios of the metal ingredients in the composite oxide catalysts and the results of oxidation reaction at a reaction temperature of 310° C. are shown in Table 5.

Comparative Experiment Example 8

100 g of bismuth nitrate and 25 g of calcium nitrate were dissolved in ion exchange water acidified with nitric acid. Also, 42 g of sodium carbonate was dissolved in ion exchange water while heating. These two solutions were gradually mixed together while agitating. After agitating and mixing, the white precipitate obtained was washed, filtered and dried. The Ca and Na contents of the bismuth subcarbonate obtained, which contained Ca, were 0.30 wt % and 0.45% respectively.

Except that the above bismuth subcarbonate powder containing Ca was used instead of the bismuth subcarbonate containing halogens described in Experiment Example 6, a composite oxide catalyst was prepared in the same manner as in Experiment Example 6 and oxidation reaction of propylene was carried out. The composition ratios of the metal ingredients of the composite oxide catalyst and the oxidation reaction results at a reaction temperature of 310° C. are shown in Table 5.

(Results)

As will be apparent from the results of Experiment Example 3 and Comparative Experiment Example 6, by adding Cl to the composite oxide catalysts, it was possible to improve the propylene conversion by 0.3% without influencing the selectivity.

Also, as is apparent from the results of Experiment Example 7 and Comparative Experiment Example 7, by adding Cl to the composite oxide catalyst, it was possible to improve the propylene conversion by 0.8% while suppressing lowering of selectively, so that it was possible to improve the total yield by 0.4%.

Further, as will be apparent from the results of Experiment Example 8 and Comparative Experiment Example 8, by adding Cl to the composite oxide, it was possible to improve the selectivity by 0.3% and the propylene conversion by 0.2%, so that it was possible to improve the total yield by 0.5%.

Further, effects similar to those in Experiment Example 8 were confirmed in Experiment Examples 9-12 too.

TABLE 4

| | Composition of catalyst (atomic ratio) | | | | | | | | | | | | | |
|---|---|---|---|---|---|---|---|---|---|---|---|---|---|---|
| | Mo | Bi | Co | Ni | Fe | Na | Mg | Ca | Zn | Ce | Sm | B | K | Cl | Si |
| EEI* 6 | 12 | 5 | 2 | 3 | 0.4 | 0.4 | — | — | — | — | — | 0.2 | 0.08 | 0.02 | 24 |
| EEI* 7 | 12 | 5 | 2 | 3 | 0.4 | 0.1 | 0.4 | — | — | — | — | 0.2 | 0.08 | 0.01 | 24 |
| EEI* 8 | 12 | 5 | 2 | 3 | 0.4 | 0.35 | — | 0.1 | — | — | — | 0.2 | 0.08 | 0.01 | 24 |
| EEI* 9 | 12 | 5 | 2 | 3 | 0.4 | 0.35 | 0.2 | — | — | — | — | 0.2 | 0.08 | 0.01 | 24 |
| EEI* 10 | 12 | 5 | 2 | 3 | 0.4 | 0.35 | — | — | 0.06 | — | — | 0.2 | 0.08 | 0.01 | 24 |
| EEI* 11 | 12 | 5 | 2 | 3 | 0.4 | 0.35 | — | — | — | 0.03 | — | 0.2 | 0.08 | 0.01 | 24 |
| EEI* 12 | 12 | 5 | 2 | 3 | 0.4 | 0.35 | — | — | — | — | 0.03 | 0.2 | 0.08 | 0.01 | 24 |
| CEE** 6 | 12 | 5 | 2 | 3 | 0.4 | 0.4 | — | — | — | — | — | 0.2 | 0.08 | — | 24 |
| CEE** 7 | 12 | 5 | 2 | 3 | 0.4 | 0.1 | 0.4 | — | — | — | — | 0.2 | 0.08 | — | 24 |
| CEE** 8 | 12 | 5 | 2 | 3 | 0.4 | 0.35 | — | 0.1 | — | — | — | 0.2 | 0.08 | — | 24 |

*Experiment Example according to the Invention
**Comparative Experiment Example

TABLE 5

| | Propylene conversion | Acrolein selectivity | Acrylic acid selectivity | Yield of acrolein | Yield of acrylic acid | Total yield |
|---|---|---|---|---|---|---|
| EEI* 6 | 99.0 | 91.9 | 4.6 | 91.0 | 4.6 | 95.6 |
| EEI* 7 | 98.9 | 92.9 | 2.4 | 91.9 | 2.4 | 94.3 |
| EEI* 8 | 99.2 | 92.2 | 4.3 | 91.5 | 4.3 | 95.8 |
| EEI* 9 | 99.2 | 92.7 | 3.6 | 92.0 | 3.6 | 95.6 |
| EEI* 10 | 99.0 | 93.5 | 2.9 | 92.6 | 2.9 | 95.5 |
| EEI* 11 | 99.3 | 91.9 | 4.2 | 91.3 | 4.2 | 95.5 |
| EEI* 12 | 99.2 | 91.7 | 4.3 | 91.0 | 4.3 | 95.3 |
| CEE** 6 | 98.7 | 91.9 | 4.5 | 90.7 | 4.4 | 95.1 |
| CEE** 7 | 98.1 | 91.6 | 4.1 | 89.9 | 4.0 | 93.9 |
| CEE** 8 | 98.9 | 91.7 | 4.7 | 90.7 | 4.6 | 95.3 |

*Experiment Example according to the Invention
**Comparative Experiment Example

TABLE 6

| | Cl Content (wt %) | Na content (wt %) | Kind | Content (wt %) |
|---|---|---|---|---|
| EEI* 9 | 0.09 | 0.45 | Mg | 0.3 |
| EEI* 10 | 0.09 | 0.45 | Zn | 0.3 |
| EEI* 11 | 0.06 | 0.45 | Ce | 0.3 |
| EEI* 12 | 0.06 | 0.45 | Sm | 0.3 |

*Experiment Example according to the Invention
**Comparative Experiment Example

<Effect Confirmation Experiments as to Use of Mo/Si Incorporated Dispersion>

Experiment Example 13

94.1 g of ammonium paramolybdate was dissolved into 400 ml of pure water under heating. Next, 64 g of Aerosil (made by Nippon Aerosil) was added into 256 ml of pure water and agitated. These two solutions (slurry) were gradually mixed and agitated sufficiently until they turn pale yellow to obtain a water dispersion. Next, 8.97 g of ferric nitrate, 32.3 g of cobalt nitrate and 32.3 g of nickel nitrate were dissolved into 60 ml of ion exchange water under heating, and the mixture was gradually mixed into the above water dispersion and agitated. To this mixture, solution in which 1.69 g of borax and 0.45 g of potassium nitrate were dissolved into 40 ml of ion exchange water while heating was added and sufficiently agitated.

Next, 100 g of bismuth nitrate was dissolved into ion exchange water acidified with nitric acid. Also, 42.0 g of sodium carbonate was dissolved into ion exchange water while heating. These solutions were gradually mixed together while sufficiently agitating. After mixing by agitating, the white precipitate obtained was washed, filtered and dried. The Na content of the bismuth subcarbonate obtained was 0.53 wt %.

34.7 g of this white bismuth subcarbonate, in which was composited 0.53 wt % of Na, was added to the above mixture and agitated and mixed. Next, after this slurry has been heated and dried, it was subjected to thermal treatment at 300° C. for an hour in an aerial atmosphere. The particulate solid obtained was formed into tablets having a diameter of 5 mm and a height of 4 mm by the use of a small molder. Next, calcining was carried out at 500° C. for four hours in a muffle furnace to form a catalyst.

The composition ratios of the metal ingredients of the catalyst calculated from the raw materials used was as follows.

Mo:Bi:Co:Ni:Fe:Na:B:K:Si=12:3:2.5:2.5:0.5:0.4:0.4:0.1:24

Oxidation reaction of propylene was carried out at the reaction temperature of 310° C. by charging 20 ml of this catalyst into a reaction tube with a jacket for a nitrate heating media and having an inner diameter of 15 mm and made of stainless steel, and passing a raw material gas having 10% of propylene concentration, 17% of steam concentration and 73% of air concentration under atmospheric pressure with the contact period at 2.0 seconds. The reaction results shown in Table 7 were obtained.

Comparative Experiment Example 9

94.1 g of ammonium paramolybdate was dissolved into 400 ml of ion exchange water while heating. Next, 8.97 g of ferric nitrate, 32.3 g of cobalt nitrate and 32.3 g of nickel nitrate were dissolved into 60 ml of ion exchange water under heating. These solutions were gradually mixed together by sufficiently agitating. To this mixture, solution in which 1.69 g of borax and 0.45 g of potassium nitrate were dissolved into 40 ml of ion exchange water while heating was added and sufficiently agitated. Next, 58.1 g of the white bismuth subcarbonate used in Experiment Example 13, in which 0.53 wt % of Na was composited, was added, and further slurry in which 64 g of Aerosil (made by Nippon Aerosil) was added to 256 ml of pure water and agitated was added, and agitated and mixed.

Next, after this slurry has been heated and dried, it was subjected to thermal treatment at 300° C. for an hour in an aerial atmosphere. The particulate solid obtained was formed into tablets having a diameter of 5 mm and a height of 4 mm by the use of a small molder. Next, calcining was carried out at 500° C. for four hours in a muffle furnace to form a catalyst. The composition ratios of the metal ingredients of the catalyst calculated from the raw materials used was as follows.

Mo:Bi:Co:Ni:Fe:Na:B:K:Si=12:3:2.5:2.5:0.5:0.4:0.4:0.1:24

Oxidation reaction of propylene was carried out at the reaction temperature of 310° C. by charging 20 ml of this catalyst into a reaction tube with a jacket for a nitrate heating media and having an inner diameter of 15 mm and made of stainless steel, and passing a raw material gas having 10% of propylene concentration, 17% of steam concentration and 73% of air concentration under atmospheric pressure with the contact period at 2.0 seconds. The reaction results shown in Table 7 were obtained.

TABLE 7

| | Propylene conversion (%) | Acrolein selectivity (%) | Acrylic acid selectivity (%) | Yield of acrolein (%) | Yield of acrylic acid (%) | Total yield (%) |
|---|---|---|---|---|---|---|
| EEI* 13 | 98.6 | 93.7 | 3.4 | 92.4 | 3.4 | 95.8 |
| CEE** 9 | 98.1 | 94.5 | 2.5 | 92.7 | 2.5 | 95.2 |

*Experiment Example according to the Invention
**Comparative Experiment Example (Results)

As will be apparent from the results of Experiment Example 13 and Comparative Experiment Example 9, by using a predetermined Mo/Si incorporated dispersion, it was possible to improve the propylene conversion by about 0.5%, improve the total of the acrolein selectivity and the acrylic acid selectivity by about 0.1%, and improve the total yield by 0.6%.

<Confirmation Experiment of Effect when Aggregated Particles have been Subjected to Dispersion Treatment>

Experiment Example 14

94.1 g of ammonium paramolybdate was dissolved into 400 ml of ion exchange water under heating. Next, 8.97 g of ferric nitrate, 32.3 g of cobalt nitrate and 32.3 g of nickel nitrate were dissolved into 60 ml of ion exchange water under heating. These solutions were gradually mixed together while agitating. To this mixture, 64 g of Aerosil (made by Nippon Aerosil) was added and agitated. The aqueous suspension obtained was subjected to dispersion treatment for 20 minutes in a homogenizer (LK-21, made by YAMATO). The aggregated particles in the dispersion thus subjected to dispersion treatment had an average particle diameter of 0.6 μm. The average particle diameter of the aggregated particles in the dispersion was measured with LMS-24 made by Seishin Enterprise.

Next, 100 g of bismuth nitrate was dissolved into ion exchange water acidified with nitric acid. Also, 42.0 g of sodium carbonate was dissolved into ion exchange water under heating. These solutions were gradually mixed together while agitating. After agitating and mixing, the white precipitate obtained was washed, filtered and dried. The Na content of the bismuth subcarbonate obtained which contained Na was 0.53 wt %.

Next, to the aqueous suspension after the dispersion treatment, a solution in which 1.69 g of borax and 0.45 g of potassium nitrate were dissolved into 40 ml of ion exchange water under heating was added and sufficiently agitated. Further, 34.7 g of the above bismuth subcarbonate which contained Na was added and sufficiently agitated and mixed under the atmospheric pressure. Next, after the slurry had been heated and dried, it was subjected to thermal treatment at 300° C. for an hour in an aerial atmosphere. The particulate solid obtained was formed to tablets having a diameter of 5 mm and a height of 4 mm by the use of a small molding machine, and next, it was calcined in a muffle furnace at 500° C. for four hours to obtain a composite oxide catalyst.

The composition ratios of the metal ingredients of the composite oxide catalyst calculated from the raw materials was as follows.

Mo:Bi:Co:Ni:Fe:Na:B:K:Si=12:3:2.5:2.5:0.5:0.4:0.4:0.1:24

Oxidation reaction of propylene was carried out by charging 20 ml of this composite oxide catalyst into a reaction tube with a jacket for a nitrate heating media and having an inner diameter of 15 mm and made of stainless steel, and passing a material gas having 10% of propylene concentration, 17% of steam concentration and 73% of air concentration at atmospheric pressure with the contact period at 2.0 seconds. At a reaction temperature of 310° C., the reaction results shown in Table 8 were obtained.

Comparative Experiment Example 10

Except that dispersion treatment using a homogenizer (LK-21 made by YAMATO) was not carried out, a composite oxide catalyst was prepared in the same manner as in Experiment Example 14, and oxidation reaction of propylene was carried out. The composition ratios of the metal ingredients of the composite oxide catalyst calculated from the raw material was as follows.

Mo:Bi:Co:Ni:Fe:Na:B:K:Si=12:3:2.5:2.5:0.5:0.4:0.4:0.1:24

Also, the reaction results at a reaction temperature of 310° C. was as follows:

(Results) As will be apparent from the results shown in Experiment Example 14 and Comparative Experiment Example 10, by carrying out dispersion treatment, it was possible to improve the propylene conversion by about 0.9% while substantially keeping the acrolein selectivity and the acrylic acid selectivity, so that it was possible to improve the total yield by about 0.7%.

TABLE 8

|  | Propylene conversion (%) | Acrolein selectivity (%) | Acrylic acid selectivity (%) | Yield of acrolein (%) | Yield of acrylic acid (%) | Total yield (%) |
|---|---|---|---|---|---|---|
| EEI* 14 | 98.5 | 92.3 | 4.7 | 90.9 | 4.6 | 95.5 |
| CEE** 10 | 97.6 | 92.5 | 4.6 | 90.3 | 4.5 | 94.8 |

*Experiment Example according to the Invention
**Comparative Experiment Example

<Effect Confirmation Experiment When Fumed Silica was Subjected to Dispersion Treatment>

Experiment Example 15

The aqueous suspension in which 320 g of Aerosil (made by Nippon Aerosil) was added to 1280 ml of ion exchange water so as to be suspended was subjected to dispersion treatment for 20 minutes in a homogenizer (LK-21 made by YAMATO). The fumed silica dispersion after dispersion treatment had an average particle diameter of 0.3 μm. The average particle diameter of the fumed silica dispersion was measured with LMS-24 made by Seishin Enterprise.

94.1 g of ammonium paramolybdate was dissolved into 400 ml of ion exchange water under heating. Next, 8.97 g of ferric nitrate, 32.3 g of cobalt nitrate and 32.3 g of nickel nitrate were dissolved into 60 ml of ion exchange water under heating. These solutions were gradually mixed together while sufficiently agitating. To this mixture, solution in which 1.69 g of borax and 0.45 g of potassium nitrate were added to 40 ml of ion exchange water was added and sufficiently agitated.

Next, 100 g of bismuth nitrate was dissolved into ion exchange water acidified with nitric acid. Also, 42.0 g of sodium carbonate was dissolved into ion exchange water under heating. These solutions were gradually mixed together while agitating sufficiently. After agitating and mixing, the white precipitate obtained was washed, filtered and dried. The Na content of the bismuth subcarbonate obtained which contained Na was 0.53 wt %.

Next, 34.7 g of the bismuth subcarbonate obtained, which contined Na, and 320 g of the fumed silica dispersion were added to an aqueous solution of the above supply source compound, and agitated and mixed. Next, after this slurry has been heated and dried, it was subjected to thermal treatment at 300° C. for an hour in an aerial atmosphere. The particulate solid obtained was formed to tablets having a diameter of 5 mm and a height of 4 mm by the use of a small molding machine. Next, it was calcined in a muffle furnace at 500° C. for four hours to obtain a composite oxide catalyst.

The composition ratios of the metal ingredients of the composite oxide catalyst calculated from the raw materials was as follows.

Mo:Bi:Co:Ni:Fe:Na:B:K:Si=12:3:2.5:2.5:0.5:0.4:0.4:0.1:24

Oxidation reaction of propylene was carried out by charging 20 ml of this composite oxide catalyst into a reaction tube with a jacket for a nitrate heating media and having an inner diameter of 15 mm and made of stainless steel, and passing a material gas having 10% of propylene concentration, 17% of steam concentration and 73% of air concentration at atmospheric pressure with the contact period at 2.0 seconds. At a reaction temperature of 310° C., the reaction results shown in Table 9 were obtained.

Comparative Experiment Example 11

320 g of Aerosil (made by Nippon Aerosil) was added to 1280 ml of ion exchange water so as to be suspended. The average particle diameter of the suspension was 52 μm.

Except that the suspension of Aerosil as mentioned above was used as the supply source compound for Si, a composite oxide catalyst was prepared in the same manner as in Experiment Example 15, and oxidation reaction of propylene was carried out. The composition ratios of the metal ingredients of the composite oxide catalyst calculated from the raw materials was as follows.

Mo:Bi:Co:Ni:Fe:Na:B:K:Si=12:3:2.5:2.5:0.5:0.4:0.4:0.1:24

The reaction results at a reaction temperature of 310° C. were as shown in Table 9.

Comparative Experiment Example 12

Except that 64 g of Aerosil (made by Nippon Aerosil) powder was used as the supply source compound for Si, a composite oxide catalyst was prepared in the same manner as in Experiment Example 15, and oxidation reaction of propylene was carried out. The composition ratios of the metal ingredients of the composite oxide catalyst calculated from the raw materials was as follows.

Mo:Bi:Co:Ni:Fe:Na:B:K:Si=12:3:2.5:2.5:0.5:0.4:0.4:0.1:24

The reaction results at a reaction temperature of 310° C. were as shown in Table 9.

TABLE 9

|  | Propylene conversion (%) | Acrolein selectivity (%) | Acrylic acid selectivity (%) | Yield of acrolein (%) | Yield of acrylic acid (%) | Total yield (%) |
|---|---|---|---|---|---|---|
| EEI* 15 | 99.0 | 95.2 | 1.6 | 94.2 | 1.6 | 95.8 |
| CEE** 11 | 98.0 | 94.7 | 2.4 | 92.8 | 2.4 | 95.2 |
| CEE** 12 | 97.9 | 95.2 | 2.1 | 93.2 | 2.1 | 95.3 |

*Experiment Example according to the Invention
**Comparative Experiment Example (Results)

As will be apparent from Experiment Example 12 and Comparative Experiment Examples 11 and 22, by using predetermined fumed silica, it was possible to improve the propylene conversion by 1.0-1.1% while substantially keeping the acrolein selectivity and the acrylic acid selectivity, so that it was possible to improve the total yield by 0.5-0.6%.

EFFECT OF THE INVENTION

As described above, according to this invention, as a catalyst used for selective reaction such as vapor phase catalytic oxidation reaction for producing acrolein or methacrolein from propylene, isobutene or tertiary butanol, vapor phase catalytic ammooxidation reaction for producing acrylonitrile or methacrylonitrile from propylene or isobutene, and vapor phase catalytic oxidative dehydrogenation reaction for producing butadiene from butene, it is possible to provide a catalyst which has improved catalytic performance such as the raw material conversion and selectivity.

The invention claimed is:

1. A process for producing a composite oxide catalyst expressed by the following formula (1):

$$Mo_aBi_bCo_cNi_dFe_eX_fY_gZ_hSi_iO_j \quad (1)$$

wherein X is at least one element selected from the group consisting of magnesium (Mg), calcium (Ca), zinc (Zn), cerium (Ce), samarium (Sm) and halogen, Y is at least one element selected from the group consisting of sodium (Na), potassium (K), rubidium (Rb), cesium (Cs) and thallium (Tl), Z is at least one element selected from the group consisting of boron (B), phosphorus (P), arsenic (As) and tungsten (W), the letters a to j are atomic ratios of the respective elements, where if a=12, then b=0.5-7, c=0-10, d=0-10 (where c–d=1-10), e=0.05-3, f=0-2, g=0.04-2, h=0-3 and i=5-48, and j is a numeral which satisfies the oxidation state of the other elements, by a process comprising incorporating supply source compounds of the respective elements into a composite in an aqueous solution, and subjecting the composite to heat treatment, comprising a pre-step for producing a catalyst precursor by mixing, while stirring, respective aqueous salt solutions of molybdenum equivalent to partial atomic ratio ($a_1$) of the entire atomic ratio (a) of molybdenum, iron, nickel and cobalt to obtain a first mixture, adding silica to the first mixture, stirring the first mixture, drying the first mixture and subjecting the first mixture to heat treatment, and an after-step in which said catalyst precursor is dispersed in an aqueous salt solution of molybdenum equivalent to the remaining atomic ratio ($a_2$) after subtracting said $a_1$ from the entire atomic ratio (a) of molybdenum, thereafter a bismuth compound is added and stirred to obtain a second mixture, and the second mixture is dried and calcined, wherein the ignition loss of said catalyst precursor is 0.5-5 wt %

Ignition loss (%)=[$W_0-W_1$]/$W_0$]×100

$W_0$: weight (g) of said catalyst precursor after drying for three hours at 150° to remove adhering water content $W_1$: weight (g) of said catalyst precursor after the adhering water content has been removed and after it has further been heat-treated for two hours at 500°.

2. A process for producing a composite oxide catalyst as claimed in claim 1 wherein $a_1$ is 1<$a_1$/(c+d+e)<3, and $a_2$ is 0<$a_2$/b<8.

3. A process for producing a composite oxide catalyst as claimed in claim 1 wherein dispersion treatment is applied to aggregated particles in an aqueous suspension to which a supply source compound for silicon is added.

4. A process for producing a composite oxide catalyst as claimed in claim 3 wherein the average particle diameter of the aggregated particles in the aqueous suspension is 0.1-10 µm.

5. A process for producing a composite oxide catalyst as claimed in claim 1 wherein the heating temperature during the step of producing the catalyst precursor is 200-400°.

6. A process for producing a composite oxide catalyst as claimed in claim 1 wherein in integrating the catalyst precursor and the bismuth compound in an aqueous solvent, ammonium water is added.

7. A process for producing a composite oxide catalyst as claimed in claim 1 wherein the elements of X, Y and Z are added during the step of producing the catalyst.

8. A process for producing a composite oxide catalyst as claimed in claim 1 wherein the calcining temperature during the catalyst producing step is in the range of 450-650°.

9. A process for producing a composite oxide catalyst as claimed in claim 1 wherein 10-100 wt % of the molybdenum supply source compound is a water dispersion obtained by integrating a molybdenum-containing compound and a silicon-containing compound in an aqueous solution.

10. A process for producing a composite oxide catalyst as claimed in claim 9 wherein said silicon-containing compound is fumed silica.

11. A process for producing a composite oxide catalyst as claimed in claim 1 wherein in producing a composite oxide catalyst containing at least molybdenum and silicon by a process comprising incorporating supply source compounds for the respective elements into a composite in an aqueous solution, and subjecting the composite to heat treatment, as at least part of the supply source compound for silicon, fumed silica is used, and the fumed silica is dispersed into aggregated particles in an aqueous dispersion to supply it in a state in which they are dispersed to an average particle diameter of 0.1-5 µm.

12. A process for producing a composite oxide catalyst as claimed in claim 1 wherein as a supply source for bismuth, at least one of bismuth oxide and bismuth subcarbonate is used, and heat treatment is conducted at 450-650°.

13. A process for producing a composite oxide catalyst as claimed claim 1 wherein as a supply source for bismuth, bismuth subcarbonate which contains at least part of required sodium in the form of a solid solution is used.

14. A process for producing a composite oxide catalyst as claimed in claim 1 wherein as a supply source for bismuth, a composite carbonate compound of bismuth containing at least part of the X component is used.

15. A process for producing a composite oxide catalyst as claimed in claim 1 wherein as a supply source for bismuth, a composite carbonate compound of bismuth containing at least part of required sodium and the X component is used.

* * * * *